US012233261B2

(12) United States Patent
Gruba et al.

(10) Patent No.: US 12,233,261 B2
(45) Date of Patent: Feb. 25, 2025

(54) EXPANDABLE ELECTROPORATION DEVICES AND METHODS OF USE

(71) Applicant: Boston Scientific Scimed, Inc., Maple Grove, MN (US)

(72) Inventors: Sarah M. Gruba, Vadnais Heights, MN (US); James A. Klos, Bay City, WI (US); James P. Rohl, Prescott, WI (US); Sandra L. Weeda, Scandia, MN (US); Troy A. Giese, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 622 days.

(21) Appl. No.: 17/459,592

(22) Filed: Aug. 27, 2021

(65) Prior Publication Data

US 2022/0062632 A1 Mar. 3, 2022

Related U.S. Application Data

(60) Provisional application No. 63/072,565, filed on Aug. 31, 2020.

(51) Int. Cl.
*A61N 1/32* (2006.01)
*A61M 25/10* (2013.01)
*A61N 1/05* (2006.01)

(52) U.S. Cl.
CPC .............. *A61N 1/327* (2013.01); *A61M 25/10* (2013.01); *A61N 1/05* (2013.01); *A61M 2025/105* (2013.01); *A61M 2205/054* (2013.01)

(58) Field of Classification Search
CPC ................ A61N 1/3787; A61N 1/3605; A61N 1/37229; H01F 38/14; H01F 27/006; H02J 50/12; H02J 50/005
See application file for complete search history.

(56) References Cited

U.S. PATENT DOCUMENTS

| 2009/0259274 A1* | 10/2009 | Simon .................. A61N 1/0517 607/42 |
| 2012/0259269 A1* | 10/2012 | Meyer ................... A61M 25/10 604/21 |
| 2013/0090649 A1* | 4/2013 | Smith ................ A61B 18/1492 606/41 |
| 2015/0066023 A1* | 3/2015 | Anderson .......... A61B 18/1492 606/41 |
| 2020/0085483 A1 | 3/2020 | Tegg et al. |
| 2020/0205890 A1 | 7/2020 | Harlev et al. |

OTHER PUBLICATIONS

International Search Report issued in International Application No. PCT/US2021/048000 dated Jan. 4, 2022 (11 pages).

* cited by examiner

*Primary Examiner* — Amanda K Hulbert
*Assistant Examiner* — Natasha Patel
(74) *Attorney, Agent, or Firm* — Bookoff McAndrews, PLLC

(57) ABSTRACT

A medical system includes a shaft having a proximal end and a distal end, a balloon attached to the distal end of the shaft, the balloon movable between an expanded state and a deflated state where a maximum diameter of the balloon is greater in the expanded state than in the deflated state, and an electrode is attached to the shaft where a portion of the balloon includes a plurality of apertures fluidly connecting an interior of the balloon to an exterior of the balloon.

18 Claims, 6 Drawing Sheets

EXPANDABLE ELECTROPORATION DEVICES AND METHODS OF USE

CROSS-REFERENCE TO RELATED APPLICATIONS

This patent application claims the benefit of priority under 35 U.S.C. § 119 to U.S. Provisional Patent Application No. 63/072,565, filed Aug. 31, 2020, which is herein incorporated by reference in its entirety.

TECHNICAL FIELD

The present disclosure relates generally to endoscopic medical devices and methods of use. More particularly, in some embodiments, the disclosure relates to endoscopic medical tools and methods related to accessing target sites and applying energy to the target sites.

BACKGROUND

Medical tools for applying energy to target tissue, for example to ablate tissue, may include a probe to heat tissue to destroy the tissue. In some instances, the shape of the probe generally does not conform to the size and/or shape of the targeted tissue. Drawbacks of many endoscopic procedures using such tools include, for example, damaging and/or destroying non-targeted tissue. Many conventional tools also do not conform to the size and shape of the target site, and may be inadequate for certain target sites, such as sphincters, the trigone region of the bladder, or other anatomical regions of the body. If the target site does not match the size of the probe, or if the target site is a shape other than a shape of the probe (e.g., an ellipsoid), the tool must be moved to different locations of the target site to damage or completely destroy the targeted tissue. Movement of the tool can result in ablating non-targeted tissue and/or causing trauma to tissue surrounding the target site. The present disclosure may solve one or more of these problems or other problems in the art. The scope of the disclosure, however, is defined by the attached claims and not the ability to solve a specific problem.

SUMMARY OF THE DISCLOSURE

According to an aspect, a medical system includes a shaft having a proximal end and a distal end, a balloon attached to the distal end of the shaft, the balloon configured to move between an expanded state and a deflated state wherein a maximum diameter of the balloon is greater in the expanded state than in the deflated state, and at least one electrode attached to the shaft, wherein a portion of the balloon includes a plurality of apertures fluidly connecting an interior of the balloon to an exterior of the balloon.

The at least one electrode may include a first electrode and a second electrode, wherein the first electrode may be positioned outside the balloon, and wherein the second electrode may be positioned inside the balloon.

The first electrode may have a pole different from a second electrode.

A distance between at least one aperture of the plurality of apertures and the first electrode may be approximately 1 cm to approximately 4 cm.

The first electrode may include a pair of first electrodes, wherein one of the pair of first electrodes may be positioned distal of a distalmost end of the balloon, and wherein the other of the pair of first electrodes may be positioned proximal of a proximal-most end of the balloon.

The balloon may include a first layer of material and a second layer of material, and wherein the second layer of material may be disposed on an outer surface of the first layer of material.

The second layer of material may form a fluid impermeable region on the outer surface of the first layer.

The second layer of material may be provided only in a fluid impermeable region of the balloon, and wherein the apertures may be exposed on the outer surface of the balloon in a fluid permeable region of the balloon.

The shaft may include a lumen extending from the proximal end of the shaft to the balloon, and wherein the lumen may be fluidly coupled to the balloon.

A fluid supply may be configured to be attached to the proximal end of the shaft, and wherein the fluid supply may be configured to supply the fluid to the balloon.

The fluid may include one or more of a saline solution and a medicament.

An electrical generator may be configured to supply a direct current to the at least one electrode in a pulsed manner.

Approximately 10 to approximately 200 pulses of direct current may be supplied to the electrode in a burst, wherein approximately 1 burst to approximately 100 bursts may be supplied to the electrode, and wherein each of the pulses may be supplied for approximately 1 µs to approximately 100 µs.

The shaft may include an outer shaft and an inner shaft, wherein a proximal end of the balloon may be attached to the outer shaft and a distal end of the balloon may be attached to the inner shaft, and wherein relative movement of the inner shaft and the outer shaft may be configured to change a distance between the proximal end of the balloon and the distal end of the balloon.

The shaft may include an inner shaft disposed within a lumen of an outer shaft, and wherein the inner shaft may be configured to translate relative to the outer shaft.

According to another aspect, a medical system includes a shaft including a proximal end and a distal end, a balloon configured to be fluidly connected to the proximal end of the shaft, a first electrode having a first polarity, wherein the first electrode is disposed within the balloon, and a second electrode connected to the shaft, wherein the second electrode includes a second polarity different from the first polarity.

The second electrode may include a pair of second electrodes, wherein one of the pair of second electrodes may be disposed proximal of a proximal-most end of the balloon, and wherein the other of the pair of second electrodes may be disposed distal of the distalmost end of the balloon.

The shaft may include an inner shaft received within a lumen of an outer shaft, wherein a proximal end of the balloon may be connected to a distal end of the outer shaft, wherein a distal end of the balloon may be attached to a distal end of the outer shaft, and wherein relative movement between the inner shaft and the outer shaft may be configured to change a length of the balloon along a longitudinal axis of the shaft.

According to yet another aspect, a medical system includes a shaft, a pair of first electrodes disposed on the shaft and configured to receive an electrical energy, a second electrode disposed on the shaft and configured to receive the electrical energy, and a balloon including a fluid permeable region and a fluid impermeable region, wherein a voltage differential is configured to be formed between the fluid permeable region and the pair of first electrodes when the electrical energy is supplied to the first electrode and the second electrode.

The pair of first electrodes may include a proximal first electrode and a distal first electrode, wherein the proximal first electrode may be disposed proximal to the fluid permeable region, wherein the distal first electrode may be disposed distal to the fluid permeable region, wherein a first voltage differential may be formed between the proximal first electrode and the fluid permeable region, and wherein a second voltage differential may be formed between the distal first electrode and the fluid permeable region.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
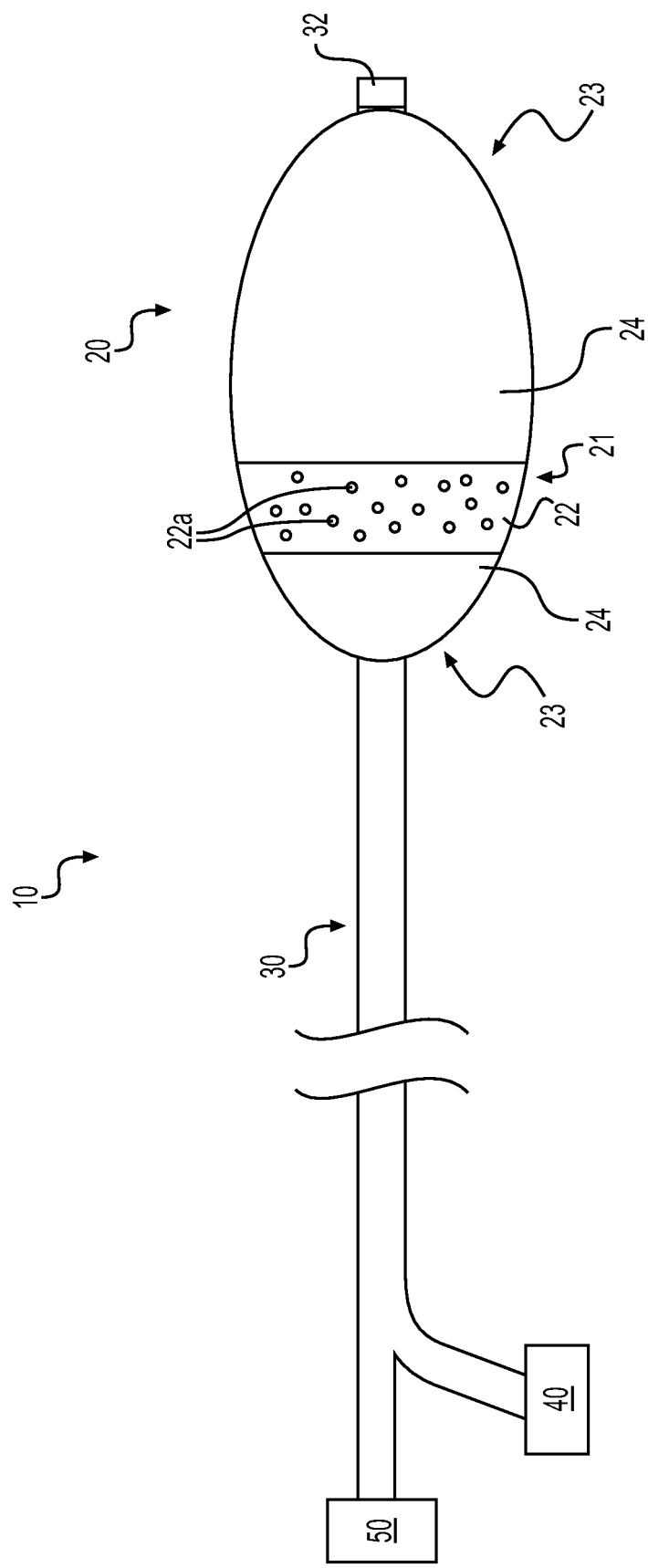
FIG. 1 is a perspective view of a medical system, according to an embodiment.

The present disclosure is described with reference to an exemplary medical system and medical tool for accessing a target site and applying energy to target tissue to, for example, damage or otherwise destroy the target tissue. However, it should be noted that reference to any particular procedure is provided only for convenience and not intended to limit the disclosure. A person of ordinary skill in the art would recognize that the concepts underlying the disclosed device and application method may be utilized in any suitable procedure, medical or otherwise. The present disclosure may be understood with reference to the following description and the appended drawings, wherein like elements are referred to with the same reference numerals.

For ease of description, portions of the device and/or its components are referred to as proximal and distal portions. It should be noted that the term "proximal" is intended to refer to portions closer to a user of the device, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface refer only to approximate shapes. For example, an expandable element that is described as having an arc shape or a helical shape indicates that the expandable element has a generally arc or a generally helical shape (e.g., the expandable elements may not form a perfect arc or helix).

Referring to FIG. 1, a medical system 10 according to an embodiment is shown. Medical system 10 includes a shaft (e.g., a flexible sheath or catheter) 30 and a balloon 20 at a distal end of shaft 30. System 10 may also include a fluid supply 40 and an electrical generator 50, each of which may be attached to a proximal end of shaft 30. For example, shaft 30 may have a Y-shape and/or may include multiple input ports at the proximal end to receive fluid supply 40 and electrical generator 50.

According to an example, electrical generator 50 may supply direct current (e.g., electrical voltage) to balloon 20 and/or the distal end of shaft 30, as will be described herein. For example, electrical generator 50 may be directly connected to wires 52, 54 (FIG. 2) at the proximal end of shaft 30, and wires 52, 54 may be attached to a first electrode 32 and a second electrode 34, respectively, at the distal end of shaft 30. Alternatively, electrical generator 50 may be attached to wires 52, 54 via a connector. For example, the connector may be attached to a side of shaft 30.

Alternatively, shaft 30 may include a handle or other actuation device at the proximal end and the connector for connecting electrical generator 50 to wires 52, 54 may be formed on or within the handle. First electrode 32 may be a single (e.g., at least one) electrode, or first electrode 32 may include multiple electrodes. Second electrode 34 may be a single (e.g., at least one) electrode, or second electrode 34 may include multiple electrodes.

Electrical generator 50 may generate a waveform, e.g., a pulsed DC current for irreversible electroporation. According to an example, electrical generator 50 may generate the irreversible electroporation (IRE) waveform, e.g., a direct current, to cause irreversible electroporation to tissue at a target site. IRE is a tissue ablation technique that uses electrical fields to create permanent nanopores in a cell membrane of a tissue, thereby disrupting the cellular homeostasis and damaging or destroying the tissue. IRE may provide the direct current sufficient to generate an electrical field of approximately 600 V/cm to 100,000 V/cm, and in some embodiments an electrical field of approximately 1,000 V/cm to 3,000 V/cm. The direct current may be applied for more than approximately 10 pulses to approximately 200 pulses, each pulse lasting approximately 1 µs to approximately 100 µs. The pulses may be supplied together in bursts, with approximately 1 burst to approximately 100 bursts supplied to the electrode. In some embodiments approximately 100 bursts are supplied, with approximately 40 pulses supplied for each burst, and each pulse lasting approximately 2 µs to approximately 10 µs. The number of pulses per treatment varies according to the size of the tissue to be treated, for example a tumor. For example, an impedance of the target tissue may be monitored to determine when the therapy is completed.

In some instances, the electrical field may be insufficient to destroy the tissue (i.e., reversible electroporation). For example, when the voltage applied per centimeter of tissue is low, e.g., 600 V/cm, the tissue may only be damaged by forming holes in the cell walls of the tissue. These holes may heal over time such that the tissue is not destroyed. As will be described herein, however, the holes created by electroporation may be large enough for fluids, e.g., drugs, medicaments, or other agents, to enter the cells. These drugs may be cancer related drugs or other drugs that may destroy the cell from the inside of the cell. Accordingly, as will be described herein, the target tissue may be exposed to a fluid including one or more drugs that may enter the cells through holes in the cell walls created by IRE, thereby destroying the cells even if the electric field is low.

With continued reference to FIG. 1, fluid supply 40 may supply fluid to balloon 20. The fluid may be any medical grade fluid, e.g., a saline solution including water, having approximately 0.9% sodium chloride by weight, and having a pH of approximately 5.5. The fluid is not limited thereto, and any saline sufficient for conducting electricity may be used, according to a medical therapy being performed. The fluid may be supplied from fluid supply 40 via a fluid lumen 36 and a fluid opening 36a (FIG. 2) to balloon 20. The fluid may be used to inflate balloon 20 at the target site. The fluid may also include drugs or other agents, e.g., cancer drugs, reagents, and/or medicaments. When introduced to balloon 20, the fluid may act as a conductor of electricity from second electrode 34 to a tissue at the target site, as will be described herein. Alternatively, or additionally, a saline/contrast mixture (e.g., a 50% saline and a 50% contrast mixture) may be supplied to inflate balloon 20 to aid in visualization of balloon 20 during the procedure.

With continued reference to FIG. 1, balloon 20 includes a fluid permeable region 21 (e.g., a first region) and fluid impermeable regions 23 (e.g., a second region) on either side of the fluid permeable region 21. It will be understood that there may be multiple fluid permeable regions 21 and/or only a single fluid impermeable region 23.

Fluid permeable region 21 includes a porous layer 22 (e.g., an inner layer) having a plurality of apertures 22a. Porous layer 22 may be formed by electrospinning a polymer or other suitable material over a mold. The electrospun polymer forms apertures 22a, having varying diameters of approximately 600 nm to approximately 3000 nm. In some embodiments, the size of apertures 22a change based on an inflation amount of balloon 20. For example, a negative charged cube of ice or a cube of ice which is electrically grounded may be rotated and may receive positively charged polymer fibers during electrospinning. The polymer fibers may be attracted to the negatively charged cube of ice and may form porous layer 22 on an outer surface of the cube of ice. Once formation of porous layer 22 is complete, the ice may be allowed to melt. Apertures 22a may be large enough to allow the water from the melted ice to pass through porous layer 22. An additional advantage of using ice to form porous layer 22 of balloon 20 may include the various shapes, e.g., cylindrical, spherical, cuboidal, asymmetrical, or any other shape suitable for balloon 20. According to an example, a distance between permeable region 21 and first electrode 32 measured along shaft 30 may be approximately 1 cm to approximately 4 cm, and measured along balloon 20 is approximately 1 cm to approximately 7 cm.

Figure 2:
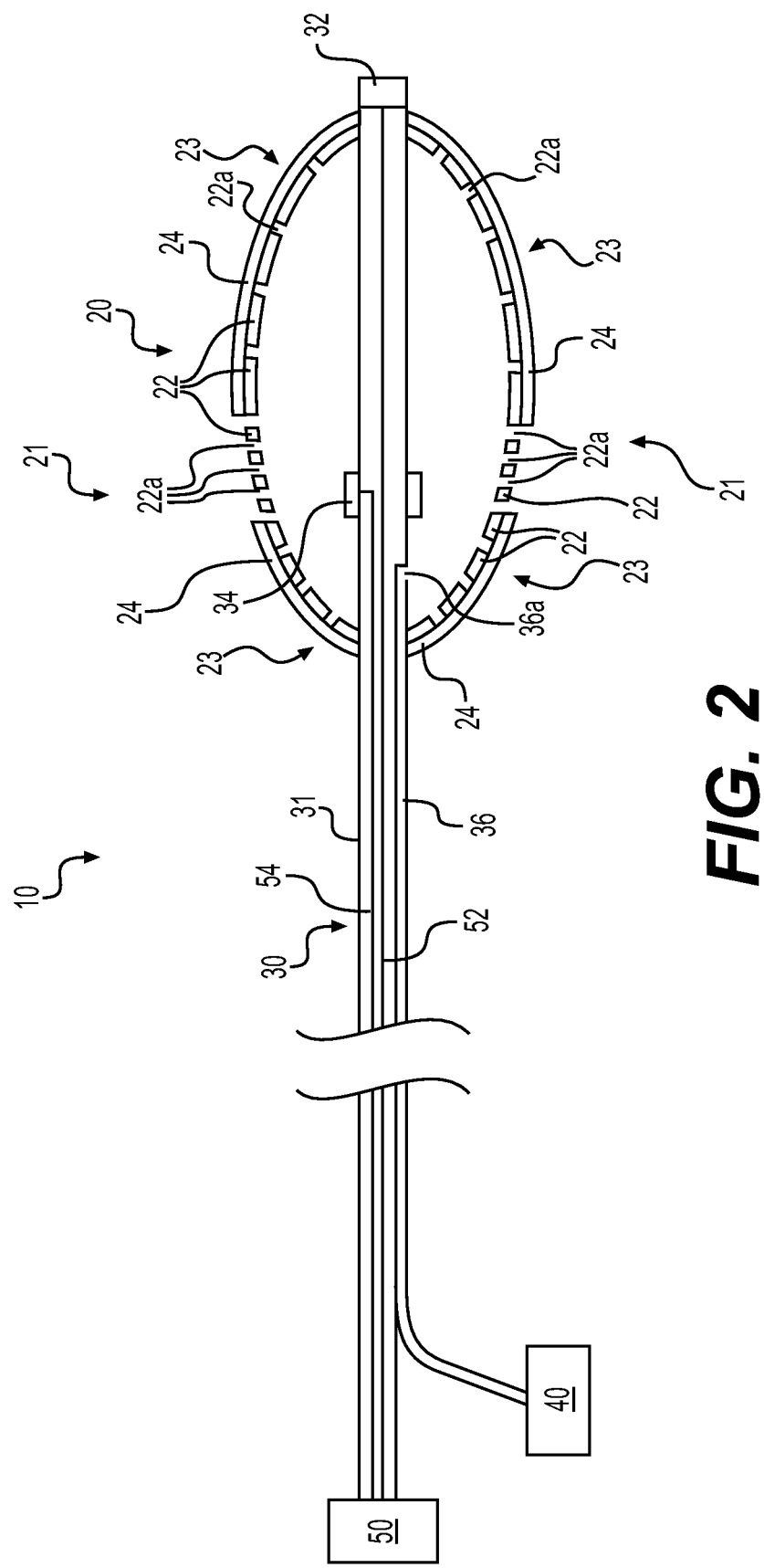
FIG. 2 is a cross-section along a plane parallel to a longitudinal axis of a shaft of the medical system of FIG. 1.

As shown in FIG. 2, fluid impermeable region 23 may include a non-porous layer 24 attached to a radially outer surface of porous layer 22. Non-porous layer 24 may include, for example, a silicone material or other material suitable for medical use, impermeable to fluid, and non-conductive. Non-porous layer 24 may be adhered to or may be formed over porous layer 22 in impermeable regions 23 to fluidly seal apertures 22a. In this manner, fluid may be released from balloon 20 only through fluid permeable region 21. Additionally, or alternatively, an outer layer of one or both of porous layer 22 or non-porous layer 24 may be coated with a drug, medicament, or other agent. In this manner, the drug or agent may be released to tissue at the target site via, e.g., drug elution, when balloon 20 is inflated during an IRE procedure, as will be described herein.

With continued reference to FIG. 2, first electrode 32 is positioned at or adjacent a distal end of shaft 30, and distal of balloon 20. First electrode 32 may be a positive electrode, a negative electrode, or an electrical ground, and may be connected to electrical generator 50 via electrical wire 52. The position of first electrode 32 is not limited, and first electrode 32 may be placed an outer surface of balloon 20 in some examples. Further, first electrode 32 may be a ring, a solid member at a distalmost end of shaft 30, or any other shaped device.

Second electrode 34 is disposed on shaft 30 within balloon 20. Second electrode 34 may be a positive electrode, a negative electrode, or an electrical ground, and will have a pole (e.g., a positive pole or a negative pole) different from first electrode 32. Electrical wire 54 connects second electrode 34 to electrical generator 50. Second electrode 34 is shown as a generally ring-shaped member having a generally uniform outer diameter. The size and shape of second electrode 34 is not limited thereto. For example, second electrode 34 may include a plurality of arms evenly spaced about a longitudinal axis of shaft 30 which may be configured to expand outward when balloon 20 is expanded and may be collapsed against shaft 30 when balloon 20 is deflated. In some instances, the plurality of arms may include two, three, four, or more arms spaced from each other about the longitudinal axis of shaft 30 by approximately 180 degrees, approximately 120 degrees, or approximately 90 degrees, respectively.

During operation, electrical pulses may be transmitted along electrical wires 52, 54. The electrical pulses transmitted via electrical wire 54 to second electrode 34 is received by the fluid in balloon 20. The electrical pulse is then transmitted from second electrode 34 to the tissue at the target site via the fluid filling balloon 20 and weeping through apertures 22a. An electrical pathway, e.g., an electrical/voltage differential, is formed between first electrode 32 and permeable region 21. For example, the fluid conducts the electricity from second electrode 34 to the tissue. The voltage differential is then applied from first electrode 32 via the tissue until the voltage differential reaches the electricity conduct to the tissue by the fluid.

A method of performing a medical procedure using medical system 10 will now be disclosed. The distal end of medical system 10 is introduced to a body via a natural orifice, e.g., a urethra or an anus, or an incision formed in the body. During insertion, balloon 20 is in a generally collapsed state such that the cross-section of balloon 20 is reduced as compared to a cross-section of balloon 20 in an expanded state. The distal end of medical system 10 is advanced to the target site within the body. In some examples, medical system 10 may include a catheter that is pre-positioned in the body and through which shaft 30 may advance to the target site. Imaging modalities, e.g., ultrasound, a camera at a distal end of the catheter, or the like may assist in positioning balloon 20 at the target site. Additionally, fluoroscopy may be used with or without a saline and a contrast mixture (e.g., 50% saline and 50% contrast) within balloon 20) to image balloon 20 and/or electrodes 32, 34.

Once balloon 20 reaches the target site, balloon 20 may be inflated by supplying the fluid from fluid supply 40 to balloon 20. Proper positioning at the target site may be determined via fluoroscopy, ultrasound, or any other imaging technique. Additionally, or alternatively, a pressure of fluid in balloon 20 may be used to determine when balloon 20 is pressing against a tissue or when fluid is supplied to balloon 20. The fluid causes balloon 20 to expand from the generally collapsed state to the generally expanded state. In the expanded state, an outer surface of balloon 20 presses against the tissue of the target site, such that portions of permeable region 21 and/or impermeable regions 23 contact the tissue at the target site. The fluid may weep through apertures 22a in porous layer 22 of permeable layer 21 and contact the tissue at the target site. Subsequently, electrical generator 50 may be actuated to supply direct current to first and second electrodes 32, 34. In this manner, an electrical differential between first electrode 32 and permeable region 21 may be generated. It will be understood that electrical generator 50 may be actuated before the fluid begins to weep from balloon 20. In some instances, the fluid may be replaced by a second, different fluid having different fluid properties during the medical procedure. For example, the second fluid may include cancer drugs or reagents and/or may contain a different amount of sodium chloride or other electrically conductive material to provide additional therapeutic effects to the tissue at the target site. After the procedure is complete, electrical generator 50 may be deactivated and balloon 20 may be withdrawn from the body. A vacuum tube may be connected to lumen 36 to remove fluid from balloon 20. Alternatively, the fluid in balloon 20 may be expelled by pressure on the outer surface of balloon 20 as balloon is removed from the body, thereby collapsing balloon 20.

Figure 3:
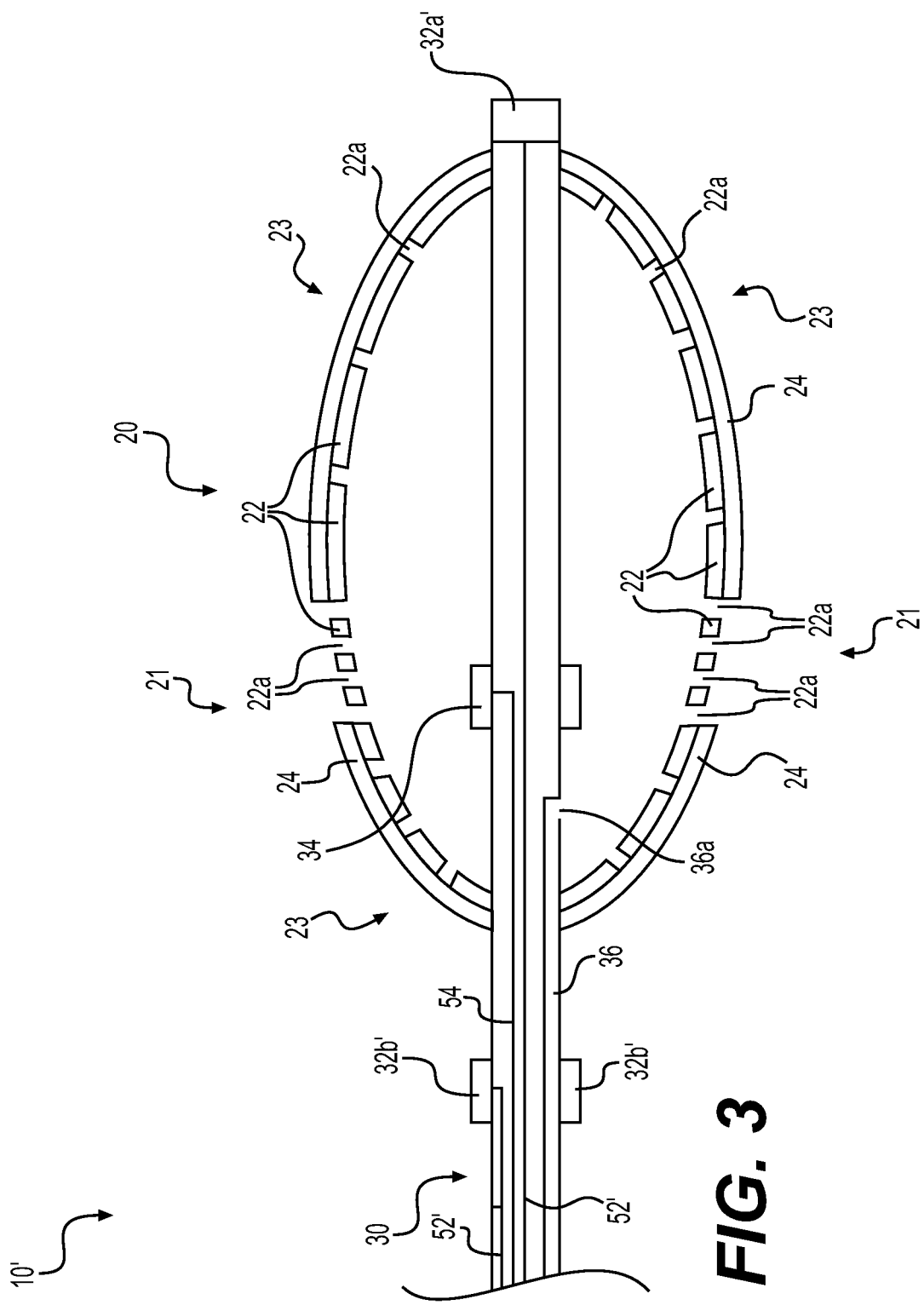
FIG. 3 is a cross-section view of a medical system along a plane parallel to a longitudinal axis of a shaft of the medical system, according to another embodiment.

A medical system 10' according to another example is shown in FIG. 3. Medical system 10' is similar to medical system 10 of FIGS. 1 and 2, having shaft 30 connected at the proximal end to electrical generator 50 and fluid supply 40. Balloon 20 is disposed at the distal end of shaft 30. A pair of first electrodes 32a', 32b' are disposed on shaft 30. One of first electrodes 32a' is disposed on shaft 30 distal of balloon 20, and the other of first electrodes 32b' is disposed on shaft 30 proximal to balloon 20. First electrodes 32a', 32b' may be connected to electrical generator 50 via electrical wires 52'. A distance between permeable region 21 and first electrode 32a' is approximately 2 cm to approximately 5 cm, or approximately 2 cm to approximately 3 cm, and a distance between permeable region 21 and first electrode 32b' is approximately 2 cm to approximately 5 cm, or approximately 2 cm to approximately 3 cm. The orientation of first electrodes 32a', 32b' relative to permeable region 21 decreases the distance between first electrodes 32a', 32b' and permeable region 21, thereby increasing the voltage per distance. For example, a same amount of voltage applied between permeable region 21 and first electrodes 32a', 32b' spaced apart by a shorter distance may allow the same amount of voltage to be supplied from electrical generator 50 (e.g., 3,000 V) while increasing the voltage applied per distance, which may improve the destruction of cells using IRE (e.g., 6,000 V/cm may provide greater cell destruction).

Medical system 10' may be operated in a similar manner as medical system 10. For example, medical system 10' may be advanced to and deployed at the target site in any manner described herein. Balloon 20 may also be deployed as described herein. Electrical generator 50 may supply direct current to one or both of first electrodes 32a', 32b', and to second electrode 34. For example, continuous pulses of direct current may be supplied to second electrode 34, while pulses may be alternatingly sent to first electrode 32a' and first electrode 32b', or vice versa. According to another example, direct current pulses may be supplied to each of first electrodes 32a', 32b', and second electrode 34 at a same time. In this manner, IRE therapy may be supplied to different areas of tissue at the target site in different patterns. For example, a first electrical path may be formed between first electrode 32a' and second electrode 34, and a second electrical path may be formed between first electrode 32b' and second electrode 34. Once the medical therapies are complete, medical system 10' may be removed from the body as discussed herein.

Figure 4:
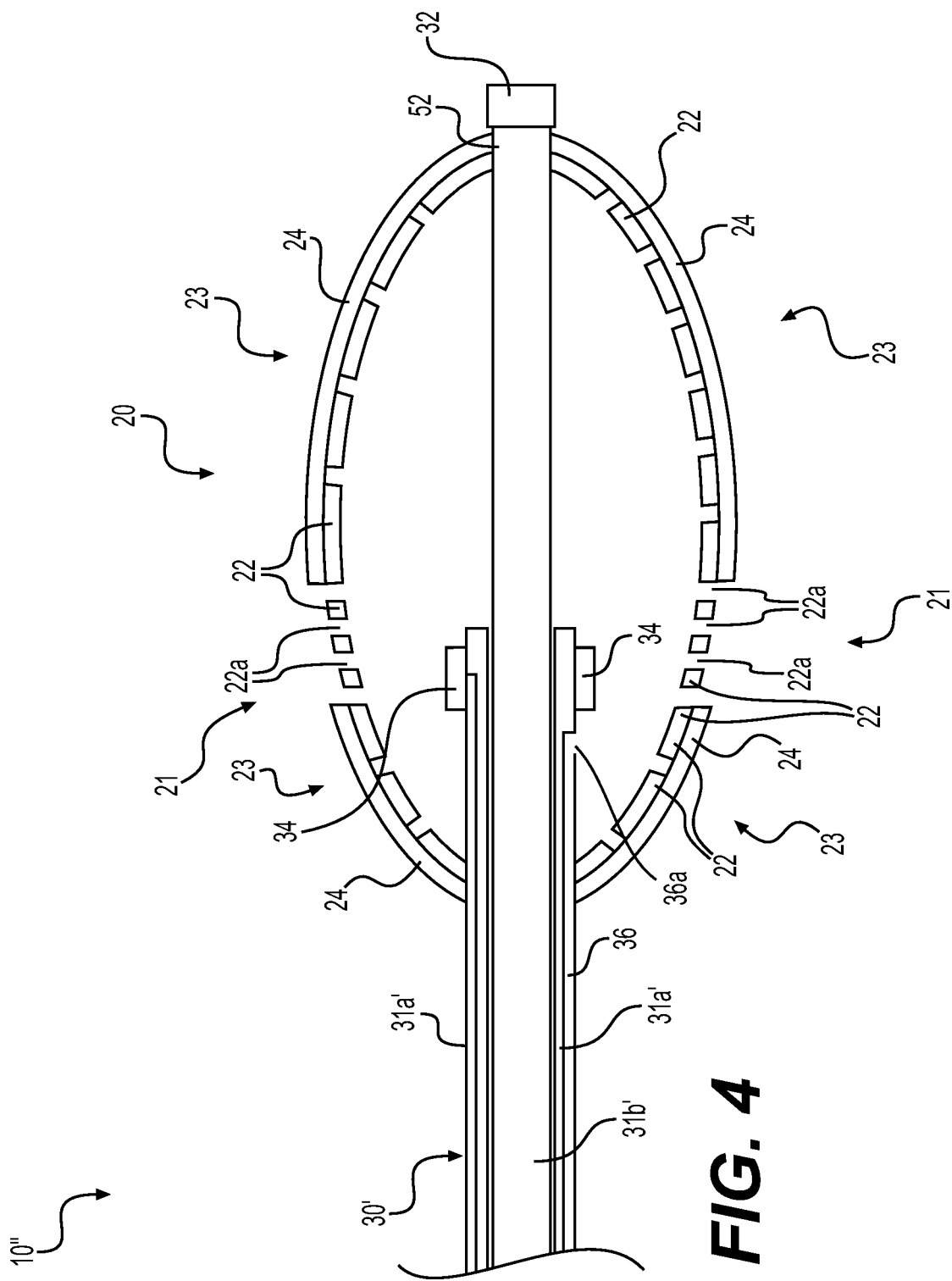
FIG. 4 is a cross-section view of a medical system along a plane parallel to a longitudinal axis of a shaft of the medical system, according to yet another embodiment.

A medical system 10" is shown in FIG. 4, and is similar to the medical system 10 of FIG. 1. Unlike shaft 30, shaft 30' includes an inner shaft 31b' configured to slide within and relative to a lumen of an outer shaft 31a'. Balloon 20 is attached at its proximal end to a distal end of outer shaft 31a', and balloon 20 is attached at its distal end to a distal end of inner shaft 31b'. First electrode 32 is disposed on an outer surface of inner shaft 31b' distal of balloon 20. Second electrode 34 may be disposed on an outer surface of outer shaft 31a' within balloon 20. A length of balloon 20 along a longitudinal axis of shaft 30 increase or decrease as inner shaft 31b' is moved relative to outer shaft 31a'. Further, a distance between first electrode 32 and permeable region 21 may be changed, which may increase or decrease the amount of voltage applied per centimeter of tissue at the target site.

Medical system 10" may be inserted into the body and advanced to the target site in the same manner as medical system 10 described herein. According to an example, outer shaft 31a' and inner shaft 31b' are moved distal at a same rate. Alternatively, inner shaft 31b' may be moved distally, which may cause outer shaft 31a', connected to inner shaft 31b' by balloon 20, to also move distally. In yet another example, outer shaft 31a' may be moved in a distal direction, which may cause inner shaft 31b' to also move distally.

Once at the target site, inner shaft 31a' and outer shaft 31b' may be moved relative to each other to elongate or shorten balloon 20. After selecting a desired length of balloon 20 along the longitudinal axis of shaft 30', the fluid from fluid supply 40 may be supplied to balloon 40. Subsequently, or simultaneously, the direct current may be applied to first electrode 32 and second electrode 34 in a pulsed manner, thereby creating an electrical field therebetween. The target site may be treated in any manner described herein with respect to medical systems 10, 10'. Once the medical therapy is complete, medical system 10" may be removed from the body as described herein.

Figure 5:
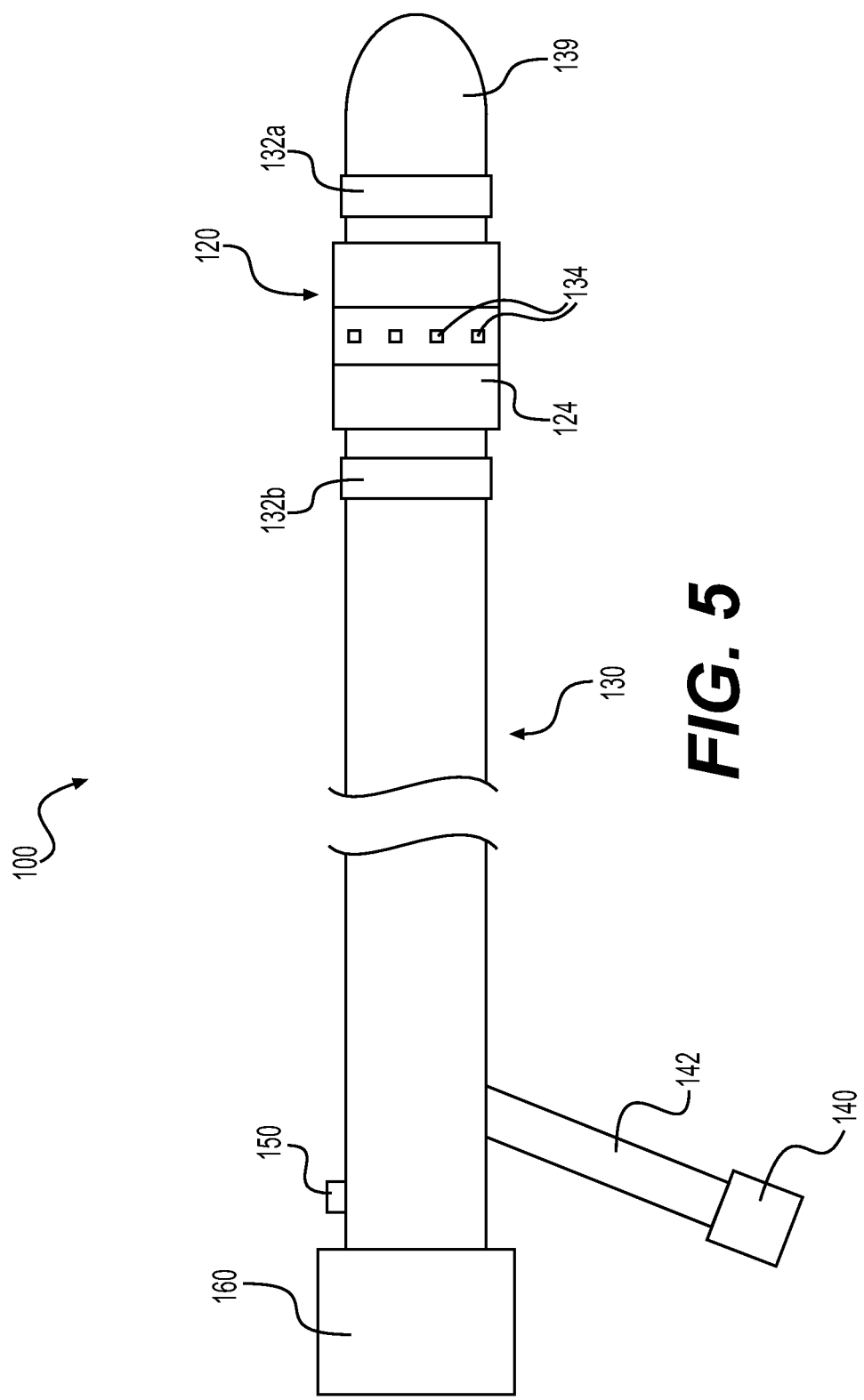
FIG. 5 is a perspective view of another medical system, according to another embodiment.
Figure 6:
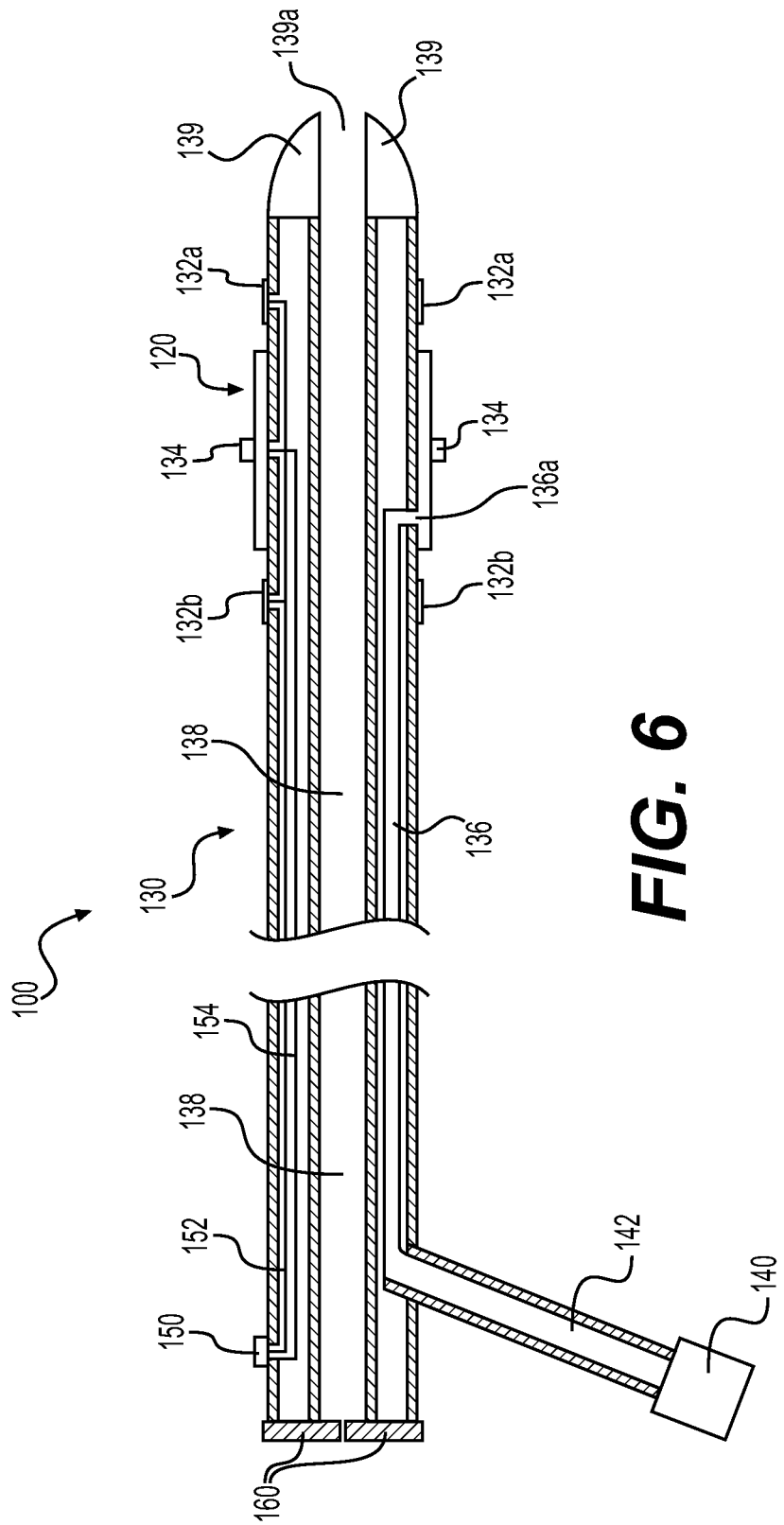
FIG. 6 is a cross-section along a plane parallel to a longitudinal axis of a shaft of the medical system of FIG. 5.

Another example of a medical system 100 according to another example is shown in FIGS. 5 and 6. Medical system 100 includes a shaft 130 having a pair of first electrodes 132a, 132b at a distal end of shaft 130 and a seal 160 at a proximal end of shaft 130. An electrical connector 150 and a fluid port 140 are also attached to the proximal end of shaft 130. Electrical connector 150 may be connected to an electrical generator, such as electrical generator 50 of FIG. 1, and fluid port 140 may be attached to a fluid supply, such as fluid supply 40 of FIG. 1. A balloon 120 may be disposed between the pair of first electrodes 132a, 132b. A distal tip 139 may be provided at the distal end of shaft 130, distal of first electrode 132a.

A cross-section of medical device 100 is shown in FIG. 6. Shaft 130 includes a central lumen 138 extending from seal 160 at the proximal end of shaft 130 to a distal opening 139a at the distal end of shaft 130. Seal 160 may be any medical grade material having flexibility to bend and seal around a medical device, e.g., a polymer-silicone composite or the like. Such a material may aid in creating a lubricious surface along which medical instruments or other devices may be readily moved. Medical instruments, suction devices, fluid supply, and any other medical device may be inserted through seal 160 and may be advanced to the distal end of shaft 130. The medical instruments or other devices may extend distally of distal opening 139a to perform medical procedures at a target site. For example, a fluid may be introduced to central lumen 138 and may be expelled from distal opening 139a to perform a medical procedure, as will be described herein. Medical opening 139a is formed in distal tip 139. Distal tip 139 is formed of a bendable and/or compressible material, e.g., silicone, which may deform when in contact with a wall of a body lumen. The deformable distal tip 139 may reduce trauma to the wall of the body lumen during insertion and/or removal of medical system 100 from the body.

As shown in FIGS. 5 and 6, balloon 120 surrounds an outer circumference of shaft 130. A plurality of second electrodes 134 are disposed about an outer circumference of balloon 120. Second electrodes 134 are connected to electrical connector 150 via an electrical wire 154. Balloon 120 is fluidly connected to fluid port 140 via a fluid lumen 136 in shaft 130 and a connection tube 142, which connects fluid port 140 to fluid lumen 136. An expansion fluid, e.g., water, air, or other medically suitable material, may be used to expand balloon 120 (it will be understood that balloon 120 is a fluidly closed system to prevent air from being released into the patient). When balloon 120 expands, second electrodes 134 disposed on balloon 120 approach and, in some instances, contact the tissue at the target site. During a medical procedure, a fluid (such as a saline solution described herein) may be supplied to the target site via central lumen 138. Balloon 120 may be expanded such that an outer surface of balloon 120 approaches tissue of the target site. For example, balloon 120 may have slack to expand. The fluid may be supplied to central lumen 138 and flow out of distal opening 139a. The fluid may then flow over shaft 130 toward the proximal end of shaft 130. As the fluid flows proximally, the fluid may flow through a space between balloon 120 and tissue at the target site, such that the fluid may contact first electrodes 132a, 132b and second electrodes 134. Applying the direct current to first electrodes 132a, 132b and second electrodes 134 causes an electrical difference between first electrode 132a and second electrode 134, and between first electrode 132b and second electrode 134. This procedure may be useful in performing a medical procedure at certain target sites within a body, e.g., the trigone region of the bladder, a sphincter, or other target sites having similar structures.

A method of performing a medical procedure using medical system 100 will now be described. Distal tip 139 may be inserted into a body via an opening, e.g., a natural orifice (an anus or a urethra) or via an incision. Distal tip 139 is advanced to the target site by moving medical system 100 in a distal direction. Once at the target site, balloon 120 may be inflated by supplying a fluid from fluid port 140 to balloon 120 via lumen 136 and connection tube 142. Once balloon 120 is expanded, a fluid (e.g., a saline fluid) may be supplied to central lumen 138. It will be understood that the fluid may include any drug and/or agent as discussed herein. Further, the fluid may be changed during the procedure, as discussed herein with respect to the method of operation of medical system 10. Subsequent to, or simultaneously with, supplying fluid to central lumen 138, the direct current may be supplied to first electrodes 132a, 132b and second electrode 134 in any method described herein. For example, alternating electrical fields may be formed between first electrode 132a and second electrode 134, and first electrode 132b and second electrode 134. Alternatively, an electrical field may be created between first electrode 132a and second electrode 134, and first electrode 132b and second electrode 134 at a same time.

After the medical procedure is complete, fluid in balloon 120 may be removed such that medical system 100 may be removed from the body. For example, a vacuum source may be attached to fluid port 140 to suction fluid from balloon 120. Alternatively, or additionally, fluid may be forced from balloon 120 toward fluid port 140 as medical system 100 is removed from the body by, e.g., pressure exerted on balloon 120 by body tissues while removing balloon 120 from the body.

The device in FIGS. 5 and 6 may also be used to ablate tissue in a patient's anatomy having a smaller volume, e.g., a urethra. For example, medical system 100 may be advanced into the urethra and balloon 120 may remain deflated, such that electrodes 132a and 132b may directly contact tissue. Current may be supplied to electrodes 132a and 132b to ablate the tissue. Once ablation is complete, medical system 100 may be moved such that a position of balloon 120 is changed within the urethra. Balloon 120 may again remain deflated and current may again be supplied to electrodes 132a and 132b to ablate tissue. In the event the cross-sectional area of the urethra is greater than the deflated balloon 120, balloon 120 may be inflated and medical system 100 may be used as described above, i.e., using inflating balloon 120 and supplying a fluid during the procedure.

Alternatively, medical system 100 may be formed without balloon 120 and second electrode 132b. For example, medical system 100 may include only shaft 130, having central lumen 138, and first electrode 132a at the distal end. Medical systems 10 or 10' (FIGS. 1, 2, and 3) may be inserted via central lumen 138 and may extend out distal opening 139a distal of distal tip 139. Balloons 20 may subsequently be expanded as described herein and may contact the wall of the body lumen. Any one of the electrodes (e.g., electrodes 32, 32a', 32b', 34, and/or 132a) may be activated to ablate the tissue. Further, fluid may be supplied via apertures in the balloons of systems 10 or 10' in the manner described herein.

It will be apparent to those skilled in the art that various modifications and variations can be made to the disclosed device without departing from the scope of the disclosure. For example, the configuration of the balloon and/or the electrodes, and/or the number of electrodes may be altered to suit any medical tool and/or target site. It will be understood that any handle suitable for use in deploying a balloon in a medical therapy may be used with the shaft, and/or the shaft may be used with any endoscope used in medical therapies. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A medical system, comprising:
  a shaft having a proximal end and a distal end;
  a balloon attached to the distal end of the shaft, the balloon configured to move between an expanded state and a deflated state, wherein a maximum diameter of the balloon is greater in the expanded state than in the deflated state, and wherein the balloon is further configured to receive a fluid from the proximal end of the shaft;
  a first electrode attached to the shaft distal of the balloon;
  a second electrode attached to the shaft proximal to the first electrode and disposed within the balloon; and
  an electrical generator configured to supply a direct current to the first electrode and the second electrode, wherein a portion of the balloon includes a fluid permeable region having a plurality of apertures fluidly connecting an interior of the balloon to an exterior of the balloon, and wherein, in response to receiving the direct current, an electrical pathway is formed between the first electrode and the fluid permeable region, and an electrical signal is transmitted from the second electrode to an environment exterior of the balloon via the fluid received by the balloon and expelled through the plurality of apertures.

2. The medical system according to claim 1, wherein the first electrode has a pole different from the second electrode.

3. The medical system according to claim 1, wherein a distance between at least one aperture of the plurality of apertures and the first electrode is approximately 1 cm to approximately 4 cm.

4. The medical system according to claim 1, wherein the balloon includes a first layer of material and a second layer of material, and wherein the second layer of material is disposed on an outer surface of the first layer of material.

5. The medical system according to claim 4, wherein the second layer of material forms a fluid impermeable region on the outer surface of the first layer.

6. The medical system according to claim 4, wherein the second layer of material is provided only in a fluid impermeable region of the balloon, and wherein the plurality of apertures are exposed on the outer surface of the balloon in the fluid permeable region of the balloon.

7. The medical system according to claim 1, wherein the shaft includes a lumen extending from the proximal end of the shaft to the balloon, and wherein the lumen is fluidly coupled to the balloon.

8. The medical system according to claim 1, further comprising a fluid supply configured to be attached to the proximal end of the shaft, and wherein the fluid supply is configured to supply the fluid to the balloon.

9. The medical system according to claim 8, wherein the fluid includes one or more of a saline solution or a medicament.

10. The medical system according to claim 1,
wherein the electrical generator is configured to supply the direct current in a pulsed manner.

11. The medical system according to claim 10, wherein the electrical generator is configured to supply approximately 10 to 200 pulses of direct current in a burst, wherein the electrical generator is configured to supply approximately 1 burst to approximately 100 bursts, and wherein the electrical generator is configured to supply each of the pulses for approximately 40 µs to 4000 µs.

12. A medical system, comprising:
a shaft including a proximal end and a distal end;
a balloon configured to be fluidly connected to the proximal end of the shaft to receive a fluid from the proximal end of the shaft, wherein a portion of the balloon includes a fluid permeable region having a plurality of apertures;
a first electrode connected to a first portion of the shaft distal of the balloon, the first electrode having a first polarity;
a second electrode connected to a second portion of the shaft proximal to the first portion of the shaft and disposed within the balloon, wherein the second electrode includes a second polarity different from the first polarity; and
an electrical generator configured to supply a direct current to the first electrode and the second electrode, wherein, in response to receiving the direct current, an electrical pathway is formed between the first electrode and the fluid permeable region, and an electrical signal is transmitted from the second electrode to an environment exterior of the balloon via the fluid received by the balloon and expelled through the plurality of apertures.

13. The medical system according to claim 12, wherein the shaft includes a lumen extending from the proximal end of the shaft to the balloon, and the balloon is fluidly connected to the proximal end of the shaft via the lumen.

14. The medical system according to claim 12, wherein the fluid permeable region is a first region of the balloon, and wherein the balloon further includes one or more second regions surrounding the first region.

15. The medical system according to claim 14, wherein the first region includes a first layer of material having the plurality of apertures exposed on an outer surface of the balloon, and each of the one or more second regions includes a second layer of material disposed on an outer surface of the first layer of material configured to fluidly seal the plurality of apertures.

16. A medical system, comprising:
a shaft including a proximal end and a distal end;
a balloon attached to the distal end of the shaft, and configured to receive a fluid from the proximal end of the shaft;
a first electrode attached to the shaft distal of the balloon;
a second electrode attached to the shaft within an interior of the balloon; and
an electrical generator configured to supply a direct current to the first electrode and the second electrode,
wherein a portion of the balloon includes a fluid permeable region having a plurality of apertures, the fluid permeable region configured to enable transmission of an electrical signal from the second electrode to an environment exterior of the balloon via the fluid received by the balloon and expelled through the plurality of apertures, and
wherein, in response to receiving the direct current, an electrical pathway is formed between the first electrode and the fluid permeable region, and the electrical signal is transmitted from the second electrode to the environment exterior of the balloon.

17. The medical system according to claim 16, wherein the second electrode is positioned proximate to the fluid permeable region within the interior of the balloon.

18. The medical system according to claim 16, wherein the fluid permeable region includes a first layer of material having the plurality of apertures, and a remainder of the balloon comprises fluid impermeable regions including a second layer of material disposed on an outer surface of the first layer of material and configured to fluidly seal the plurality of apertures.

* * * * *